United States Patent [19]

Schroeder

[11] 4,296,043
[45] Oct. 20, 1981

[54] PROCESS FOR THE PREPARATION OF BENZANTHRONES

[75] Inventor: Josef Schroeder, Leverkusen, Fed. Rep. of Germany

[73] Assignee: Bayer Aktiengesellschaft, Leverkusen, Fed. Rep. of Germany

[21] Appl. No.: 39,790

[22] Filed: May 17, 1979

[30] Foreign Application Priority Data

May 26, 1978 [DE] Fed. Rep. of Germany ....... 2823160

[51] Int. Cl.³ .............................................. C07C 50/22
[52] U.S. Cl. ................................................... 260/352
[58] Field of Search .................... 260/352; 252/431 P, 252/437

[56] References Cited

U.S. PATENT DOCUMENTS

| 820,379 | 5/1906 | Bally et al. ........................... 260/352 |
| 1,749,519 | 3/1930 | Trautner et al. ..................... 260/364 |
| 1,934,221 | 11/1933 | Wuertz ................................. 260/364 |
| 4,127,595 | 11/1978 | Matsuura et al. .................... 260/352 |

FOREIGN PATENT DOCUMENTS

| 2371413 | 6/1978 | France . |
| 178942 | 8/1935 | Switzerland . |
| 16538 | of 1904 | United Kingdom ................ 260/352 |
| 297129 | 9/1928 | United Kingdom . |

*Primary Examiner*—Winston A. Douglas
*Assistant Examiner*—Raymond K. Covington
*Attorney, Agent, or Firm*—Sprung, Felfe, Horn, Lynch & Kramer

[57] ABSTRACT

Process for the preparation of benzanthrones of the formula

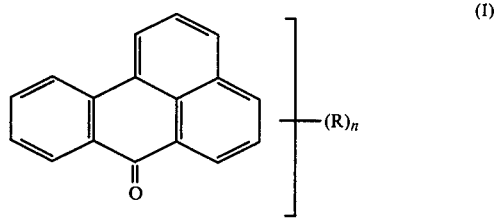

(I)

in which
R designates alkyl or halogen and
n represents 0, 1, 2 or 3, characterized in that anthraquinones of the formula

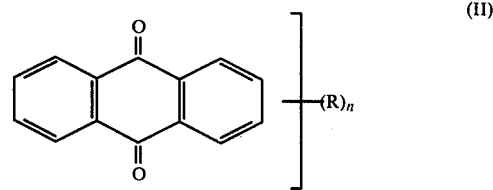

(II)

in which
R and n have the meaning indicated above, are reacted with acrolein or compounds from which acrolein can be formed under the reaction conditions, in the presence of phosphorus or phosphorus compounds having a reducing action, in relatively highly concentrated sulphuric acid at elevated temperature, and the reaction mixture is worked up in a manner which is in itself known to give the benzanthrones of the formula (I).

8 Claims, No Drawings

PROCESS FOR THE PREPARATION OF BENZANTHRONES

The invention relates to a process for the preparation of benzanthrones.

It is known that benzanthrone is formed by a conjoint reaction of anthraquinone, reducing agent and glycerol. [N. N. Woroskzow, Grundlagen der Synthese von Zwischenprodukten und Farbstoffen (Principles of the Synthesis of Intermediate Products and Dyestuffs), pages 907 et seq., Akademie-Verlag, Berlin 1966]. In the literature, metals such as iron, aluminium or copper are recommended as reducing agents.

It has now been found that benzanthrones of the formula

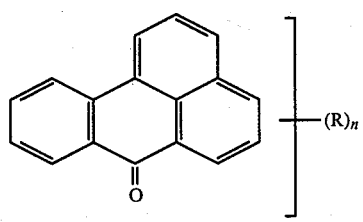
(I)

in which
R denotes alkyl or halogen and
n represents 0, 1, 2 or 3, are obtained when anthraquinones of the formula

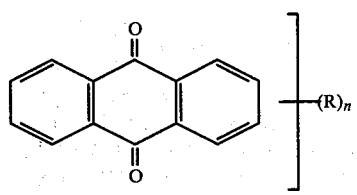
(II)

in which
R and n have the meaning indicated above, are reacted with acrolein or compounds from which acrolein can be formed under the reaction conditions, in the presence of phosphorus or phosphorus compounds having a reducing action, in relatively highly concentrated sulphuric acid at elevated temperature, and the mixture is worked up in a manner which is in itself known to give the benzanthrones of the formula (I).

The anthraquinones of the formula (II) employed as starting materials are known [see, for example, Elsevier's Encyclopedia of Organic Chemistry, Volume 13, pages 400 et seq.], or they can be prepared by processes analogous to those known from the literature.

The process is particularly suitable for the preparation of benzanthrones of the formula I in which R designates $C_1$-$C_4$-alkyl, such as methyl, ethyl, n-propyl, i-propyl, n-butyl, sec.-butyl and tert.-butyl, or halogen, such as chlorine and bromine.

n preferably represents 0, 1 or 2.

The new process is very particularly suitable for the preparation of benzanthrone itself or of compounds of the formula

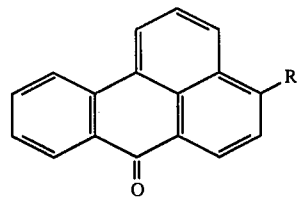
(III)

in which
R has the meaning indicated above.

The acrolein used for forming the ring can be employed as such in the reaction. However, compounds from which acrolein is formed in sulphuric acid at elevated temperature are preferably used for producing acrolein, and glycerol and also glycerol esters, such as glycerol monoacetate, diacetate and triacetate, are particularly suitable for this.

Phosphorus compounds in a low state of oxidation, preferably those in the +1 state of oxidation, and preferably in the form of the alkali metal salts of hypophosphorous acid, are employed as the reducing agents. The reduction can also be effected with phosphorous acid, and salts and esters thereof, for example trimethyl phosphite or triethyl phosphite. Elementary phosphorus is also suitable for the reduction.

Whilst 2–4 reduction equivalents are employed per mol of anthraquinone when sodium hypophosphite is used, preferably 2.5–3.5 reduction equivalents, that is to say 0.5 to 1 mol of sodium hypophosphite, per mol of anthraquinone, more than the amount corresponding to molar proportions is required when phosphorous acid, esters thereof or elementary phosphorus are used. The amounts of reducing agent to be employed can easily be determined by the expert.

The reaction mixture preferably contains 2 to 10 parts by weight, in particular 3 to 5 parts by weight, of sulphuric acid, which should be about 80 to 100% strength, per part by weight of anthraquinone compound.

The reaction is preferably carried out in a temperature range from 80° to 140° C., particularly preferably at 100° to 120° C. The reaction time is preferably 1 to 10 hours; the most favourable reaction times are 2 to 4 hours.

The process can be carried out, for example, as follows:

The anthraquinone compound of the formula (II) is dissolved in relatively highly concentrated sulphuric acid, for example 96% strength or monohydrate, at elevated temperature (about 80°–110° C.).

(a) The reducing agent, for example phosphorus, phosphorous acid and salts or esters thereof or salts of hypophosphorous acid, is now first added to this solution and acrolein or substances from which acrolein can be formed, such as, for example, glycerol or glycerol esters, are then added.

(b) A more advantageous procedure consists in dissolving suitable phosphorus compounds, such as, for example, phosphorous acid or sodium hypophosphite, in glycerol and metering in this solution at a rate depending on the progress of the reaction, which results in particular advantages in controlling the temperature.

The crude benzanthrones are obtained by pouring the reaction melts into water. After boiling up with a weak alkali, a product of high purity results, in yields of >90% of theory; in the case of low contents, the concomitant material is, for example, unreacted anthraquinone.

As can be seen from thin layer chromatograms, the conversion of anthraquinones into benzanthrones takes place with almost no side reactions.

The new process is simple to carry out; by working in a homogeneous solution, the reaction can easily be controlled. Considerable advantages compared with known processes also exist in the simple working up and isolation of the reaction products.

Large amounts of hydrogen, which are obtained when metallic reducing agents are used, do not occur.

Because the mixture is essentially more concentrated, the amount of dilute acid obtained is smaller; ecological pollution of the effluents obtained is significantly lower.

The high quality of the benzanthrones which can be prepared by the process according to the invention, which in the case of conventional processes can be achieved only by additional and expensive purification sections, such as, for example, vacuum sublimation, should also be mentioned.

The benzanthrones which can be prepared by the process according to the invention are known [see, for example, Elsevier's Encyclopaedia of Organic Chemistry, Volume 14, pages 362 et seq.], and are used as intermediate products for valuable vat dyestuffs.

EXAMPLE 1

208 g of anthraquinone are dissolved in 1,000 g of concentrated sulphuric acid at 80°–110°. 96 g of sodium hypophosphite, dissolved in 240 g of glycerol, are added to this solution in a manner such that a temperature of 100° C. can be maintained. The mixture is then heated to 120° C. and kept at this temperature for 3 hours. The melt is then poured into 3 l of water and the product which has precipitated is filtered off. It is washed with hot water until the runnings are almost colourless, the filter cake is then suspended in 1.5 l of water and the suspension is rendered weakly alkaline and boiled up. After renewed filtration of the product, washing with hot water and drying at 100° C., 200–225 g of 92–97% pure benzanthrone ≈ 80–93% of theory result.

EXAMPLE 2

The following compounds can be reacted smoothly analogously to Example 1: 2-methylanthraquinone, to give a mixture of monomethylbenzanthrones (mostly 4-methylbenzananthrone); 2-ethylanthraquinone, to give a mixture of monoethylbenzanthrones (mostly 4-ethylbenzanthrone); 1,5-dichloroanthraquinone, to give 6,10-dichlorobenzanthrone; and 2-chloroanthraquinone, to give a mixture of monochlorobenzanthrones.

The individual compounds can be isolated from the mixtures by fractional crystallisation.

I claim:

1. Process for the preparation of benzanthrone of the formula

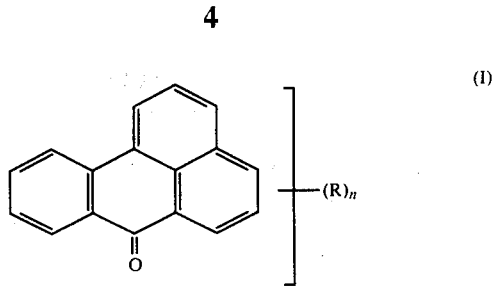

in which
R designates alkyl or halogen and
n represents 0, 1, 2 or 3,
which comprises contacting an anthraquinone of the formula

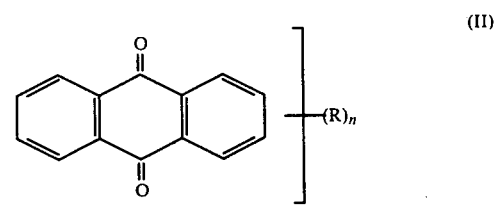

in which
R and n have the meaning indicated above, with acrolein or a compound from which acrolein is formed under the reaction conditions, in the presence of phosphorus or a phosphorus compound having a reducing action, in relatively highly concentrated sulphuric acid at elevated temperature, and working up the reaction mixture to give the benzanthrone of the formula (I).

2. Process according to claim 1, characterised in that 2 to 4 reduction equivalents of phosphorus or phosphorus compound are employed per mol of anthraquinone of the formula (II), 2 to 10 parts by weight of 80 to 100% strength sulphuric acid are employed per part by weight of anthraquinone of the formula (II), and the reaction is carried out in the temperature range from 80° to 140° C.

3. Process according to claim 1, characterised in that a compound which supplies acrolein under the reaction conditions is employed and said compound is glycerol or a glycerol acetate.

4. Process according to claim 1, characterised in that the phosphorus compound which has reducing action which is employed is sodium hypophosphite.

5. Process according to claim 1, characterised in that the reducing phosphorus compound is dissolved in glycerol and the solution is added to the reaction mixture of anthraquinone of the formula (II) and sulphuric acid.

6. A process for the preparation of a benzanthrone according to claim 1, wherein the compound of formula II is anthraquinone.

7. A process for the preparation of a benzanthrone according to claim 1, wherein a phosphorus compound having a reducing action is employed and said phosphorus compound is an alkali metal salt of hypophosphorous acid, phosphorous acid, a phosphorous acid salt or a phosphorous acid ester.

8. A process according to claim 1, wherein elementary phosphorus is present in the reaction mixture.

* * * * *